US012788228B2

(12) United States Patent
Hill et al.

(10) Patent No.: US 12,788,228 B2
(45) Date of Patent: Nov. 10, 2026

(54) MEDICAL DEVICES AND ARTICULATION JOINTS FOR MEDICAL DEVICES

(71) Applicant: Boston Scientific Scimed, Inc., Maple Grove, MN (US)

(72) Inventors: Katie Hill, Duxbury, MA (US); Elizabeth Mark, Boston, MA (US); Man Minh Nguyen, Harvard, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 233 days.

(21) Appl. No.: 18/602,400

(22) Filed: Mar. 12, 2024

(65) Prior Publication Data

US 2024/0306899 A1 Sep. 19, 2024

Related U.S. Application Data

(60) Provisional application No. 63/490,782, filed on Mar. 17, 2023.

(51) Int. Cl.
*A61B 1/005* (2006.01)
*A61B 1/008* (2006.01)

(52) U.S. Cl.
CPC .......... *A61B 1/0055* (2013.01); *A61B 1/0057* (2013.01); *A61B 1/008* (2013.01)

(58) Field of Classification Search
CPC ...... A61B 1/0055; A61B 1/0057; A61B 1/008
See application file for complete search history.

(56) References Cited

U.S. PATENT DOCUMENTS 5,555,618 A * 9/1996 Winkler ................. A61N 1/056 606/48
7,637,905 B2 * 12/2009 Saadat ................. A61B 1/0055 606/1
11,452,501 B2 * 9/2022 Cuscuna .............. A61B 8/4466
11,464,586 B2 * 10/2022 Alvarez ................ A61M 25/02
2004/0138525 A1 * 7/2004 Saadat ................. A61B 1/0055 600/104
2008/0287741 A1 * 11/2008 Ostrovsky ......... A61M 25/0141 600/141

(Continued)

FOREIGN PATENT DOCUMENTS

EP 1 819 266 B1 10/2019

*Primary Examiner* — Anhtuan T Nguyen
*Assistant Examiner* — Shankar Raj Ghimire
(74) *Attorney, Agent, or Firm* — Bookoff McAndrews PLLC

(57) ABSTRACT

An articulation joint for a medical device includes a proximal longitudinal section, a distal longitudinal section, and a locking wire. The proximal longitudinal section defines a lumen and includes proximal articulation links. Each proximal articulation link has a contact surface abutting a contact surface of an adjacent proximal articulation link when the articulation joint is in a straight configuration. The distal longitudinal section is distal to the proximal longitudinal section and includes distal articulation links configured to bend in the first direction. The locking wire extends through the lumen adjacent the contact surfaces of the proximal articulation links. A distal end of the locking wire is fixed to a distal articulation link, and tensioning of the locking wire prevents bending of the proximal longitudinal section in the first direction and allows bending of the distal longitudinal section in the first direction.

19 Claims, 5 Drawing Sheets

(56) References Cited

U.S. PATENT DOCUMENTS

| | | | | |
|---|---|---|---|---|
| 2009/0062606 | A1* | 3/2009 | Ueda | A61B 1/00078 600/114 |
| 2009/0209815 | A1* | 8/2009 | Smith | A61B 1/0055 600/149 |
| 2010/0069882 | A1* | 3/2010 | Jennings | A61M 25/0158 604/525 |
| 2011/0082337 | A1* | 4/2011 | Boulais | A61B 1/0057 600/146 |
| 2013/0060239 | A1* | 3/2013 | Hinman | A61B 17/29 606/1 |
| 2014/0094787 | A1* | 4/2014 | Reynolds | A61M 25/0138 606/41 |
| 2014/0094799 | A1* | 4/2014 | Ladtkow | A61B 18/082 606/49 |
| 2015/0230697 | A1* | 8/2015 | Phee | A61B 1/0057 901/41 |
| 2016/0029878 | A1* | 2/2016 | Yamazaki | A61B 1/0057 600/149 |
| 2017/0209227 | A1* | 7/2017 | Yoshimura | A61B 34/71 |
| 2017/0245933 | A1* | 8/2017 | Graham | A61B 17/29 |
| 2018/0042451 | A1* | 2/2018 | Cuscuna | A61B 8/12 |
| 2018/0235443 | A1* | 8/2018 | Smith | A61B 1/0055 |
| 2019/0117193 | A1* | 4/2019 | Cuscuna | A61B 8/12 |
| 2020/0046942 | A1* | 2/2020 | Alvarez | A61M 25/02 |
| 2020/0359873 | A1* | 11/2020 | Powell | A61B 1/0052 |
| 2021/0219821 | A1* | 7/2021 | Appling | A61B 1/0056 |
| 2024/0172927 | A1* | 5/2024 | Uehara | A61B 1/008 |

* cited by examiner

MEDICAL DEVICES AND ARTICULATION JOINTS FOR MEDICAL DEVICES

CROSS-REFERENCE TO RELATED APPLICATIONS

This application claims the benefit of priority under 35 U.S.C. § 119 from U.S. Provisional Application No. 63/490,782, filed Mar. 17, 2023, which is incorporated by reference herein in its entirety.

TECHNICAL FIELD

This disclosure relates generally to endoscopic medical devices and methods of use. More particularly, in some embodiments, the disclosure relates to endoscopes and related methods for accessing target sites having space constraints, using, e.g., a flexible steerable shaft such as an articulation joint at a distal end of the endoscope.

BACKGROUND

Endoscope devices generally include a flexible shaft, a working distal tip, and a flexible steerable shaft joining the working tip and the flexible shaft. The flexible steerable shaft may include a bendable articulation joint. Drawbacks of articulation joints of some conventional endoscopes include, for example, the inability to provide a suitably small bend radius and/or appropriate bend angle for the anatomy being viewed. These drawbacks can prevent the physician from properly visualizing and/or accessing areas of the body during procedures.

Accordingly, it is desirable for the articulation joint to provide an appropriate bend radius and/or bend angle when flexing the articulation joint. This disclosure may solve one or more of these problems or other problems in the art. The scope of the disclosure, however, is defined by the attached claims and not the ability to solve a specific problem.

SUMMARY OF THE DISCLOSURE

According to an example, an articulation joint for a medical device may comprise a proximal longitudinal section, a distal longitudinal section, and a locking wire. The proximal longitudinal section may define a lumen therethrough and may have proximal articulation links, each proximal articulation link having a contact surface abutting a contact surface of an adjacent proximal articulation link when the articulation joint is in a straight configuration, to limit bending of the proximal longitudinal section to only a first direction. The distal longitudinal section may be distal to the proximal longitudinal section and may have distal articulation links, wherein the distal longitudinal section is configured to bend in the first direction. The locking wire may extend through the lumen adjacent the contact surfaces of the proximal articulation links, wherein a distal end of the locking wire is fixed to a distal articulation link. Tensioning of the locking wire may prevent bending of the proximal longitudinal section in the first direction and may allow bending of the distal longitudinal section in the first direction.

In other examples, the articulation joint may include one or more of the following features. A gap may be defined between adjacent proximal articulation links, the gap being disposed on a side of the proximal longitudinal section opposite a side having the contact surfaces. A spring may connect adjacent proximal articulation links along surfaces of the adjacent proximal articulation links between the contact surfaces and the gap. A plurality of the distal articulation links may be distal of the locking wire, such that tensioning of the locking wire does not straighten or bend the plurality of the distal articulation links. The locking wire may be arranged in a zig-zig pattern within the lumen. The distal longitudinal section may bend in a second direction, a third direction, and a fourth direction. A pair of gaps may be defined between adjacent distal articulation links. The articulation joint may comprise actuation elements extending through the lumen and operable to control bending of the articulation joint. The actuation elements may comprise four wires for controlling bending of the articulation joint in the first direction, a second direction, a third direction, and a fourth direction. The articulation joint may comprise actuation holes coupled to each of the proximal articulation links and the distal articulation links, wherein the actuation elements extend through the actuation holes. The articulation joint may comprise springs defining the actuation holes. The locking wire may extend through at least one of the actuation holes. At least one of the actuation holes may accommodate the locking wire and one of the actuation elements. A maximum combined bending of the proximal longitudinal section and the distal longitudinal section in the first direction when the locking wire is not tensioned may be approximately 180 degrees, and a maximum combined bending of the proximal longitudinal section and the distal longitudinal section in the first direction when the locking wire is tensioned may be approximately 90 degrees. The proximal longitudinal section may be straight when the locking wire is tensioned.

In other examples, an articulation joint for a medical device may comprise a proximal longitudinal section, a distal longitudinal section, a locking wire, a first wire and a second wire. The proximal longitudinal section may define a lumen therethrough and may have proximal articulation links, each proximal articulation link having a flat contact surface abutting a flat contact surface of an adjacent proximal articulation link when the articulation joint is in a straight configuration, to limit bending of the proximal longitudinal section to only a first direction. The distal longitudinal section may be distal to the proximal longitudinal section and may have distal articulation links, wherein the distal longitudinal section is configured to bend in the first direction and a second direction opposite the first direction. The locking wire may extend through the lumen adjacent the contact surfaces of the proximal articulation links, wherein a distal end of the locking wire is fixed to a distal articulation link, and tensioning of the locking wire prevents bending of the proximal longitudinal section in the first direction and allows bending of the distal longitudinal section in the first direction. The first wire and the second wire may each extend through the lumen, the first wire for controlling bending of the distal longitudinal section in the first direction, and the second wire for controlling bending of the distal longitudinal section in the second direction, wherein each of the first wire and the second wire extends distally past the distal end of the locking wire.

In other examples, the articulation device may include one or more of the following features. The distal longitudinal section may be configured to bend in a third direction and a fourth direction opposite the third direction, and the articulation joint further may comprise a third wire and a fourth wire each extending through the lumen, the third wire for controlling bending of the distal longitudinal section in the third direction, and the fourth wire for controlling bending of the distal longitudinal section in the fourth direction, wherein each of the third wire and the fourth wire extends distally past the distal end of the locking wire. The locking wire may be arranged in a zig-zig pattern within the lumen.

In other examples, an articulation joint for a medical device may comprise a proximal longitudinal section, a distal longitudinal section, and a locking wire. The proximal longitudinal section may define a lumen therethrough and may have proximal articulation links, each proximal articulation link having a contact surface abutting a contact surface of an adjacent proximal articulation link when the articulation joint is in a straight configuration, to limit bending of the proximal longitudinal section to only a first direction. The distal longitudinal section may be distal to the proximal longitudinal section and may have distal articulation links, wherein the distal longitudinal section is configured to bend in the first direction and a second direction opposite the first direction. The locking wire may extend through the lumen adjacent the contact surfaces of the proximal articulation links, wherein a distal end of the locking wire is fixed to a distal articulation link, and tensioning of the locking wire prevents bending of the proximal longitudinal section in the first direction, allows bending of the distal longitudinal section in the first direction, and retains the proximal longitudinal section in a straight configuration. The proximal longitudinal section and the distal longitudinal section may combine to bend 180 degrees in the first direction when the locking wire is not tensioned. A maximum combined bending of the proximal longitudinal section and the distal longitudinal section in the first direction when the locking wire is tensioned may be approximately 90 degrees.

In other examples, the articulation joint may comprise four wires extending through the lumen and operable to control bending of the articulation joint in the first direction, the second direction, a third direction, and a fourth direction.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Figure 1:
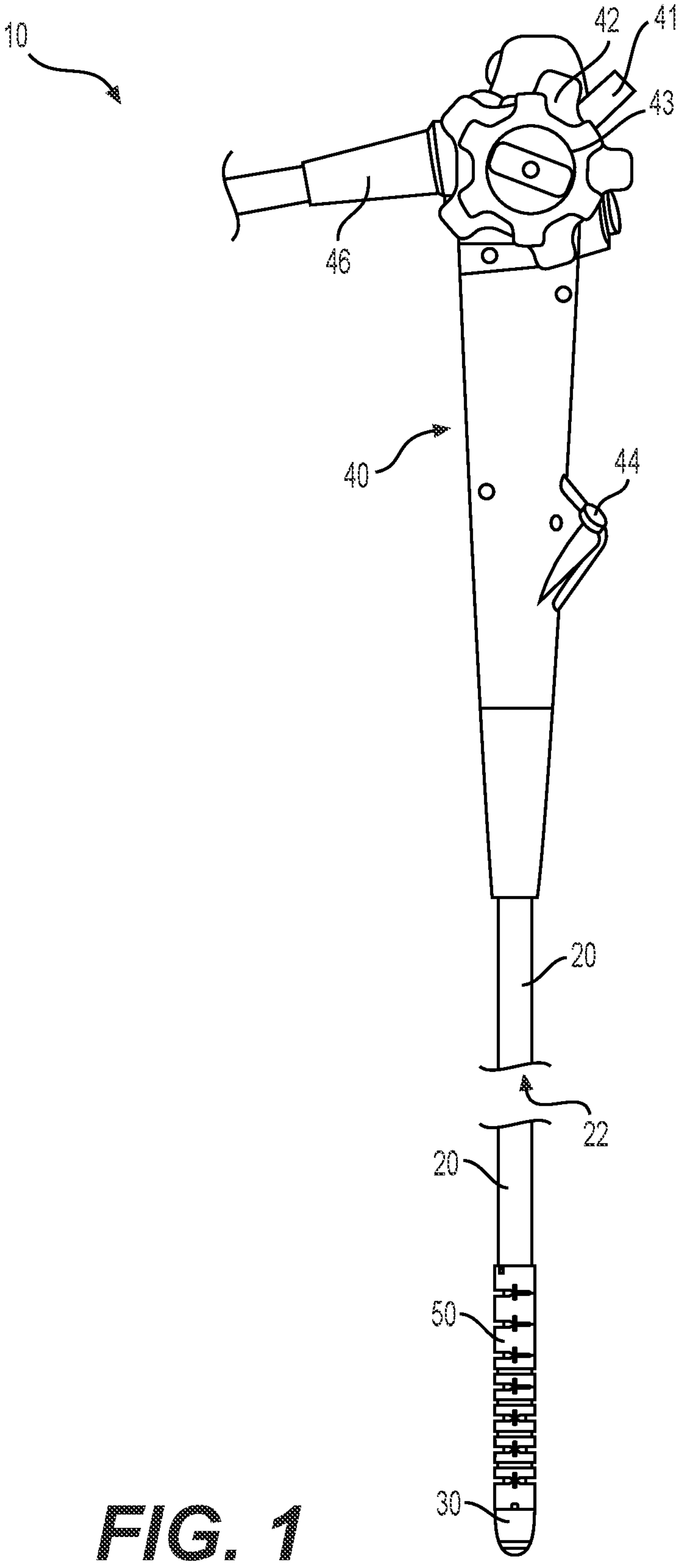
FIG. 1 is a perspective view of a medical device according to an embodiment.

Referring to FIG. 1, an endoscope 10 according to an embodiment is shown. Endoscope 10 includes a flexible shaft 20, a tip 30 at a distal end of endoscope 10, and an articulation joint 50 disposed between and connecting flexible shaft 20 and tip 30. A handle 40 or some other device for actuating or controlling endoscope 10, and any tool or devices associated with endoscope 10, is connected at a proximal end of flexible shaft 20.

Referring to FIG. 1 in combination with FIGS. 4A-4D, a plurality of actuating elements 12 and a locking wire 60 may extend distally from a proximal end of endoscope 10. The actuation elements 12 and the locking wire 60 may be any appropriate structure and material, such as cables or wires suitable for medical procedures (e.g., medical grade plastic or metal). In some embodiments, the actuation elements 12 and the locking wire 60 may be the same material, while, in other embodiments, the actuation elements 12 and the locking wire 60 may have varying materials. Actuating elements 12 and the locking wire 60 are shown between adjacent links in, e.g., FIGS. 4A-4D. Actuating elements 12 and locking wire 60 may extend into handle 40 and may be indirectly coupled to first, second, and third actuating devices 41, 42, and 43 which control articulation of articulation joint 50 in multiple directions. Devices 42, 43, may be, for example, rotatable knobs that rotate about their axes to push/pull actuating elements 12. Actuating device 41 can be any suitable actuator, including a knob, a lever, etc., for pushing/pulling/providing tension to the locking wire 60. For example, the actuating device 41 may be a rotatable lever, such as depicted. The lever may rotate clockwise or counterclockwise to push/pull the locking wire 60. In other embodiments, the actuating device 41 may be a knob, such as the actuating devices 42 and 43, and may be positioned adjacent and aligned with the axes of the actuating devices 42 and 43. Alternatively, or additionally, a user may operate actuating elements 12 and/or the locking wire 60 independently of handle 40.

Distal ends of actuating elements 12 extend through flexible shaft 20 and terminate at articulation joint 50 (at or near a distal end of articulation joint 50) and/or tip 30. For example, one or more actuating elements 12 may be connected to articulation joint 50 and one or more other actuating elements 12 may be attached to tip 30. As will be explained herein, actuation of actuating elements 12 may control articulation joint 50, tip 30, and/or elements attached to tip 30, such as an end effector (not shown). A distal end of locking wire 60 may extend through the flexible shaft 20 and terminate at articulation joint 50 (at a midpoint along joint 50, as will be described further herein). In addition, one or more electrical cables (not shown) may extend from the proximal end of endoscope 10 to tip 30 and may provide electrical controls to imaging, lighting, and/or other electrical devices on tip 30, and may carry imaging signals from tip 30 proximally to be processed and/or displayed on a display. Handle 40 may also include ports 44, 46 for introducing and/or removing tools, fluids, or other materials from the subject. Port 44 may be used to introduce tools. Port 46 may be connected to an umbilicus for introducing fluid suction, and/or wiring for electronic components.

Figure 2:
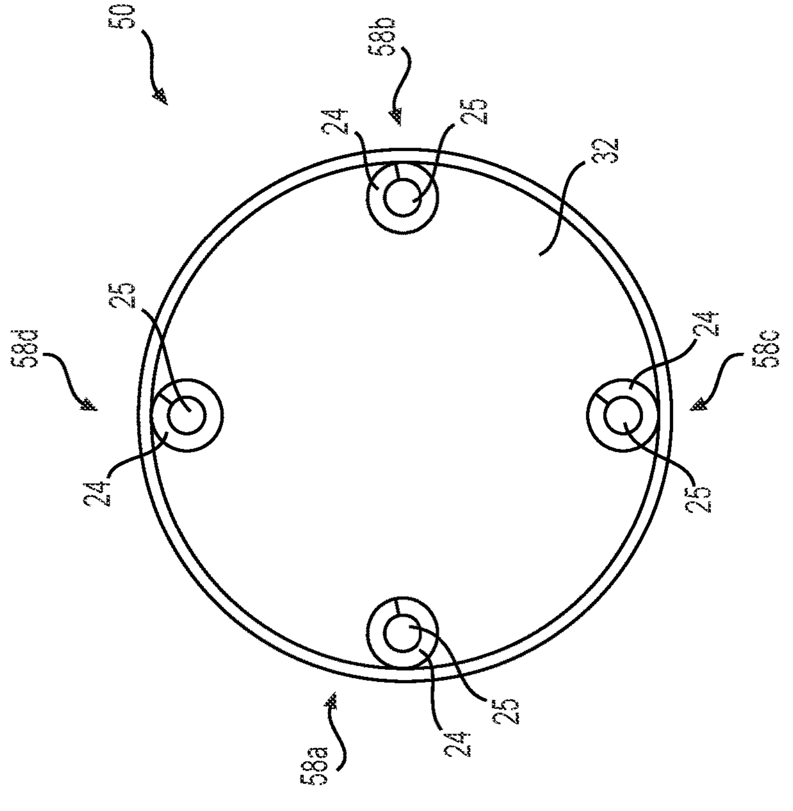
FIG. 2 is a cross-section of an articulation joint of the medical device according to FIG. 3 along the section A-A.

As shown in FIG. 2, articulation joint 50 includes a portion of an endoscope lumen 22 that extends through endoscope 10. Articulation joint 50 also includes a plurality of springs 24. For ease of understanding, only some of the plurality of springs 24 are identified in FIG. 3. Further, springs 24 have been removed in FIGS. 4A-4F for ease of understanding (springs 24 are located between pairs of laser welds 28, described below). Springs 24 connect adjacent links of articulation joint 50, as will be described in greater detail herein. Endoscope lumen 22 may extend from handle 40 through flexible shaft 20 into articulation joint 50, and through a distal end of tip 30. Endoscope lumen 22 may receive tools, imaging devices, and other devices associated with endoscope 10 to perform endoscopic procedures. Further, tissue samples and/or other material may be removed from a subject through endoscope lumen 22. It will be understood that endoscope 10, including flexible shaft 20 and articulation joint 50, are not limited to a single endoscope lumen 22, and may include any number of endoscope lumens necessary for performing procedures. Alternatively, or additionally, one or more catheters (not shown) may be introduced through endoscope lumen 22 to remove tissue and/or insert tools.

With continued reference to FIG. 2, springs 24 define actuation holes 25 through which actuation elements 12 may extend. According to an example, one actuating element 12 or a plurality of actuating elements 12 may be disposed in a single actuation hole 25 of each spring 24. Additional actuation holes, such as eyelets (not shown), may extend from a proximal end of flexible shaft 20 to a distal end thereof, and may provide a path through which actuation elements 12 may extend, thereby preventing actuating elements 12 from becoming tangled or otherwise adversely affecting an operation of endoscope 10.

Figure 3:
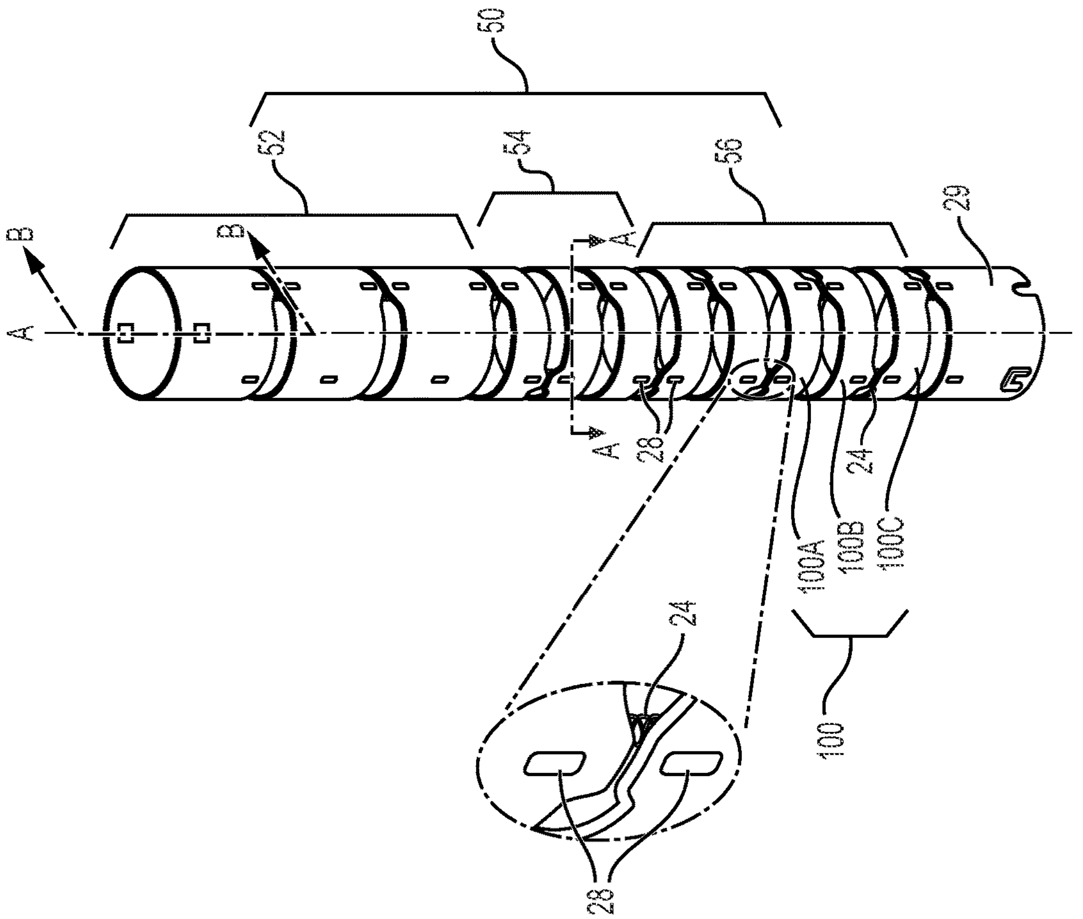
FIG. 3 is a perspective view of the articulation joint of FIG. 2.

With reference to FIG. 3, a distalmost link 29 may connect to tip 30. Tip 30 may include a camera, lighting, electronics (such as a printed circuit board), an end effector or tool (none of such elements being shown), or any other device used in a therapeutic or a diagnostic procedure. It will be understood that tip 30 may include multiple elements, e.g., both the camera and the end effector, to both visualize a target site and to collect samples from the target site.

Articulation joint 50 will be further described with reference to FIGS. 3 and 4A-4D. Articulation joint 50 includes a plurality of generally cylindrical links with a plurality of gaps provided therebetween. For example, as shown in FIG. 3, articulation joint 50 includes a first link section 52, a third link section 56, and a second link section 54 provided between and connecting the first link section 52 and the third link section 56. The plurality of links may define a lumen 32 extending therethrough. The lumen 32 may form a portion of the endoscope lumen 22 (depicted in FIG. 1). The springs 24 and the actuation holes 25 may be coupled to the plurality of links within the lumen 32.

Figure 4B:
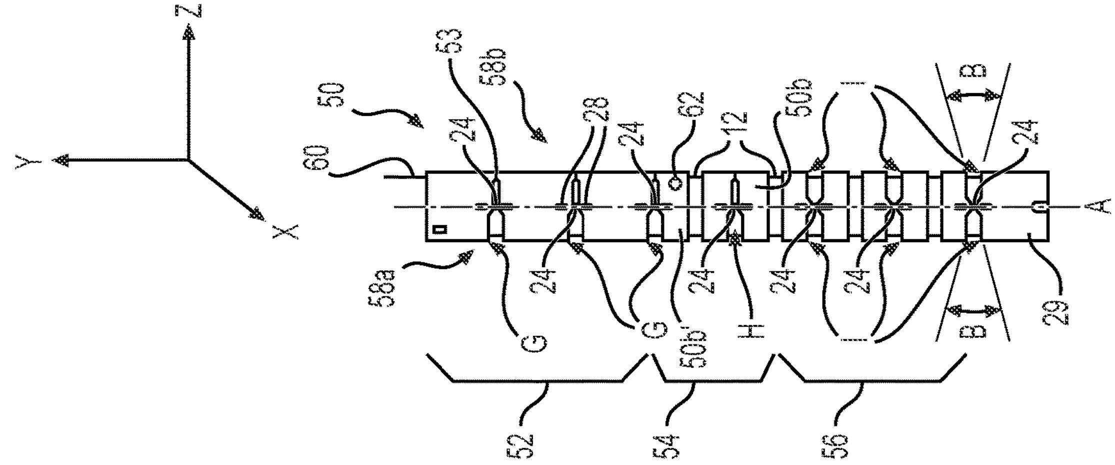
FIGS. 4A-4D are side views of the articulation joint of FIG. 3.
Figure 4A:
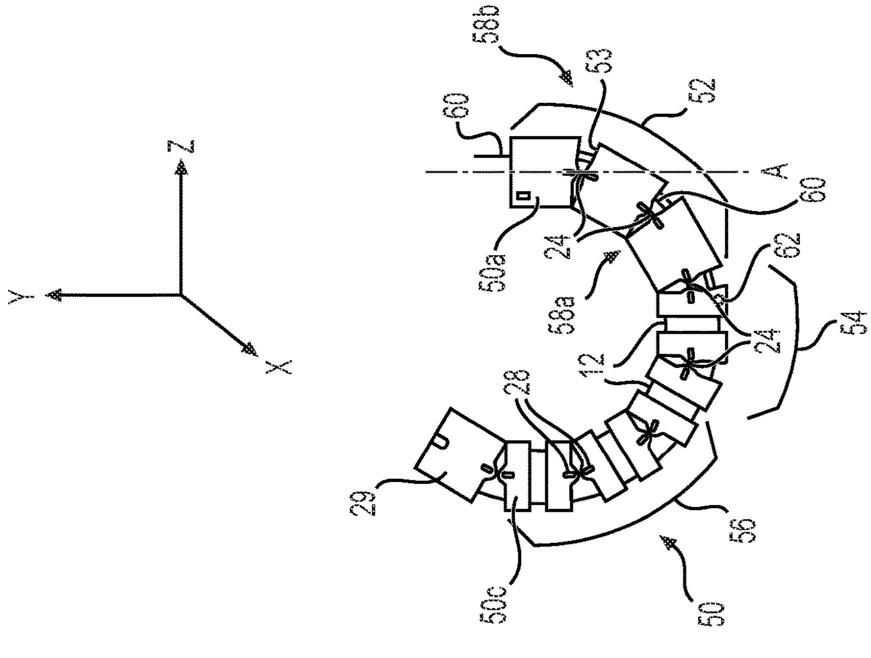
Figure 4D:
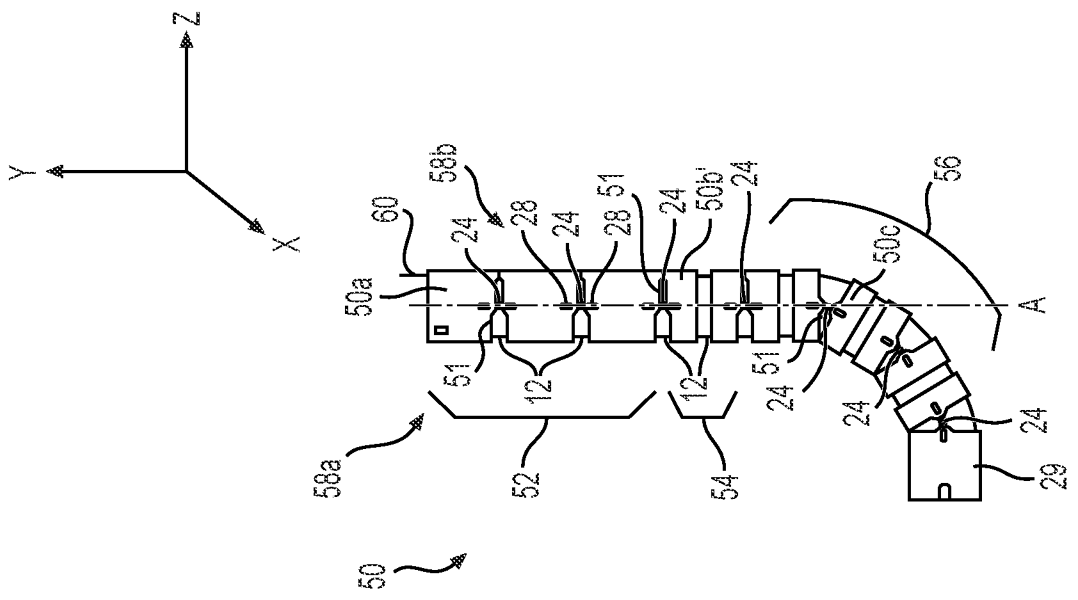
Figure 4C:
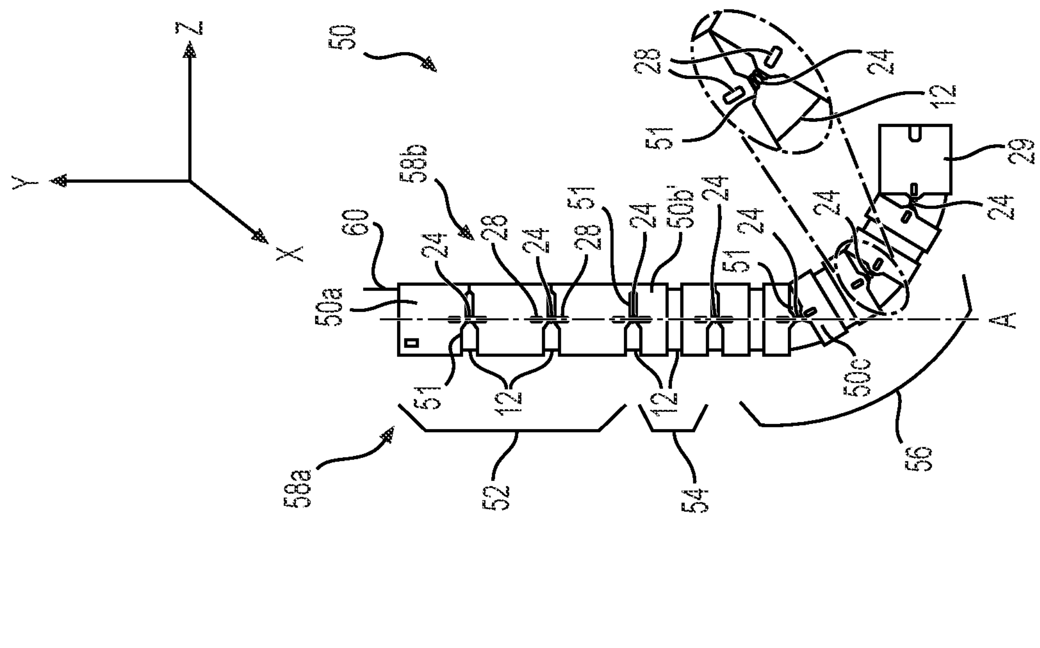

First, second, and third link sections 52, 54, 56 are formed of a first link type 50*a*, a second link type 50*b*, and a third link type 50*c*, respectively (see FIG. 4C). According to an example, first, second, and third link types 50*a*, 50*b*, 50*c* may be the same or different shapes and/or sizes. For example, first link type 50*a* is longer along longitudinal axis A than second and third link types 50*b*, 50*c*. Unless specified otherwise, first link type 50*a*, second link type 50*b*, and third link type 50*c* will generally be referred to as a "link." Links may be formed by, for example, laser cutting a tube (such as a metal tube, a plastic tube, or any other medical grade material known in the art), but are not limited to being formed in this manner. As will be described in greater detail herein, the plurality of links may include partial articulation links and full articulation links. More specifically, the first link section 52 may comprise partial articulation links, and the second link section 54 and third link section 56 may comprise full articulation links.

As further shown in FIGS. 2 and 3, springs 24 join adjacent links in each of first, second, and third link sections 52, 54, 56. Additionally, springs 24 may connect a distalmost link of first link section 52 to a proximalmost link of second link section 54, may connect a distalmost link of second link section 54 to a proximalmost link of third link section 56, and/or may connect a distalmost link of third link section 56 to distalmost link 29. As will be described in greater detail herein, adjacent links are capable of bending with respect to each other due to spacing between links and via the flexibility of springs 24. While examples illustrate two springs 24 joining adjacent links, the invention is not limited to this configuration. According to an example, springs 24 are attached to an inner surface of articulation joint 50 by, e.g., laser welding, adhesives, rivets, or any other technique known in the art. For example, laser welds 28 are shown on adjacent links in FIG. 3 at locations at which springs 24 are attached.

As shown in FIG. 4B, articulation joint 50 is in a straight configuration and includes a longitudinal axis A extending through a center of each of first, second, and third link sections 52, 54, 56. Articulation joint 50 is configured to bend in four different directions 90 degrees apart from each other about axis A (e.g., up, down, left and right directions). Referring briefly to FIG. 3 in combination with FIGS. 4A-4D, the directions of bending are designated as a first side 58*a*, a second side 58*b*, a third side 58*c* (directed into the page and depicted and labeled in FIG. 2), and a fourth side 58*d* (directed out of the page and depicted and labeled in FIG. 2), approximately 90 degrees from each adjacent side. First side 58*a* is opposite second side 58*b* (approximately 180 degrees apart), and the third side 58*c* is opposite the fourth side 58*d* (approximately 180 degrees apart). As shown in FIGS. 4A and 4C, links are bent in each of first, second, and/or third link sections 52, 54, 56 with respect to each other. Springs 24 are located on only two adjacent sides, e.g., the third side 58*c* and the fourth side, of first link section 52. As will be described in greater detail below, springs 24 are located on first, second, third, and fourth sides 58*a*, 58*b*, 58*c*, 58*d* of second link section 54 and third link section 56.

As shown in FIG. 4C, each link includes an end surface 51 facing an adjacent link. End surfaces 51 of adjacent links are in contact when articulation joint 50 is in the straight configuration. For example, contact may include point contact between adjacent end surfaces 51 at the third side 58*c* and the fourth side 58*d* of adjacent links 50*c*. For ease of understanding, only some end surfaces 51 are identified by a reference numeral in FIGS. 4A-4D. However, it will be understood that end surfaces 51 are provided at each end of every link.

Referring specifically to the first link section 52, the end surface 51 may include a flat contact surface 53. The flat contact surface 53 may be flat, or planar, in a plane perpendicular to the longitudinal axis A, such as depicted in FIGS. 4A-4D. The flat contact surface 53 may extend partially about a circumference of the adjacent links 50*a*, e.g. about a second side 58*b*. As shown particularly in FIG. 4C, the flat contact surfaces 53 of the end surfaces 51 may prevent articulation of first link section 52 toward the second side 58*b*.

Opposite the flat contact surface 53, each link of the adjacent links 50*a* may include a gap G. Accordingly, on first side 58*a* of first link section 52, end surface 51 of one link 50*a* is spaced from end surface 51 of an adjacent link 50*a*. The end surface 51 approaches end surface 51 of the adjacent link 50*a* as articulation joint 50 bends toward first side 58*a*, closing the gap G when articulation joint 50 is completely bent toward first side 58*a*, as shown in FIG. 4A.

As described above, springs 24 connect adjacent links 50*a* on only two sides, e.g., the third side 58*c* and the fourth side 58*d*. In other words, the springs 24 may be disposed between the flat contact surface 53 and the gap G. The springs 24 maintain contact between the adjacent links 50*a* on the third side 58*c* and the fourth side 58*d*. In addition, springs 24 are tightly wound coiled springs with no spaces between adjacent coils when the spring is in a straight configuration. For this reason, links having a first link type 50*a* in first link section 52 are incapable of bending toward the third side 58*c* or the fourth side 58*d*. According to an embodiment, therefore links 50*a* of first link section 52 bend in a single direction, e.g., toward first side 58*a*. It will therefore be appreciated that the adjacent links 50*a* of the first link section 52 may be considered partial articulation links.

Referring now to the second link section 54 and the third link section 56, as shown in FIGS. 4A-4D, end surface 51 of a second link 50*b* contacts end surface 51 of an adjacent link 50*b* on only one side, i.e., second side 58*b*, when articulation joint 50 is in the straight configuration. End surface 51 of third link type 50*c* does not contact end surface 51 of an adjacent link 50*c* when articulation joint 50 is in the straight configuration. When a second link 50*b* is bent toward first side 58*a*, end surface 51 of the second link 50*b* contacts end surface 51 of an adjacent second link 50*b*. When a third link 50*c* is bent toward first or second sides 58*a*, 58*b*, end surface 51 of the third link 50*c* contacts end surface 51 of an adjacent third link 50*c*. Contact between end surfaces 51 of adjacent links prevents further bending of adjacent links of articulation joint 50, and results in the maximum bend of articulation joint 50 in that specific direction.

Further, springs 24 are attached to all four sides (58*a*, 58*b*, 58*c*, 58*d*) of second link section 54 and third link section 56. The springs 24 are attached to adjacent links at offset positions, however. For example, three adjacent links 100 (see FIG. 3) include two pairs of adjacent links. The first pair of adjacent links 100A, 100B is attached together by springs 24 on first and second sides 58*a*, 58*b*, such that the first pair of adjacent links 100A, 100B are unable to be bent relative to each other toward first and second sides 58*a*, 58*b*. The second pair of adjacent links 100B, 100C is attached together via springs 24 on the third and fourth sides 58*c*, 58*d*. Second pair of adjacent links 100B, 100C are therefore unable to bend toward the third and fourth sides 58*c*, 58*d* with respect to each other due to the arrangement of springs 24. Each of the links 100A, 100B, and 100C, defines a pair of gaps between the link and the adjacent link (depicted as gaps in FIG. 4B). Taken together, the three adjacent links 100 are moveable in four directions, i.e. toward each of the four sides 58*a*, 58*b*, 58*c*, and 58*d*.

Referring back to FIGS. 4A-4D, it will therefore be appreciated that the adjacent links 50*c* of the third link section 56 may be considered full articulation links. As used herein, "full" articulation means that the link section is not prevented from articulation toward one side as the first link section 52 is prevented from articulation toward the first side 58*b*.

Referring to the articulation joint 50 as a whole, adjacent links in each of first, second, and third link sections 52, 54, 56 are capable of bending with respect to each other in at least one direction. The angle at which adjacent links may bend and the spacing between these adjacent links may be equal to a smallest bend radius at which imaging wires and other components are capable of bending and remaining functional. For example, a largest bend angle B of adjacent links spaced apart by 0.3 inches to 0.7 inches is approximately 20 degrees to 40 degrees, preferably approximately 25 degrees to 35 degrees at a 0.4 inch to 0.6 inch spacing between adjacent links, and more preferably approximately 30 degrees at a 0.5 inch spacing between adjacent links.

Referring to FIGS. 4A-4D, longitudinal axis A extends in the Y-axis, and articulation joint 50 bends in the Y-Z plane. As shown in FIG. 4B, a first gap G is provided between adjacent links within the first link section 52, and between a distalmost link in first link section 52 and a proximalmost link of second link section 54, along a first side 58*a* of articulation joint 50. A second gap H is provided between adjacent links in second link section 54 on first side 58*a*. A third gap I is provided between links in third link section 56, and between a distalmost link of third link section 56 and distalmost link 29, on both first side 58*a* and second side 58*b*.

The first, second, and third gaps G, H, I allow articulation joint 50 to bend an amount equal to bend angle B multiplied by the number of total gaps. For example, if bend angle B is 30 degrees and there are seven total gaps on first side 58*a*, articulation joint 50 may bend 210 degrees from longitudinal axis A and allow tip 30 to point toward an entry point of endoscope 10 into the subject. The size of gaps G, H, and I may be varied to achieve a desired bend angle. For example, gap H and the three gaps I may be made smaller so that the bend angle between the adjacent links defining those gaps is about 22.5 degrees. In that case, the total angle of bend of joint 50 caused by those gaps is 90 degrees. It will also be understood that the bend angles are merely examples, and the bend angle of each different gap may be different for a gap type, e.g., each different gap G from the plurality of gaps G may have a different bend angle.

According to an example, third gaps I on second side 58*b* allow adjacent links to bend at a same angle B as first gaps G. However, that angle associated with third gaps I on second side 58*b* is not limited to angle B and may be any angle that optimizes the bend angle of articulation joint 50. As shown in FIG. 4C, third gaps I allow third link section 56 and distalmost link 29 to bend away from longitudinal axis A toward second side 58*b* while first link section 52 and second link section 54 do not bend toward second side 58*b*, i.e., first link section 52 and second link section 54 remain coaxial with longitudinal axis A. This configuration allows articulation joint 50 to bend 90 degrees toward second side 58*b*. Since this bend is performed by bending at only some gaps, i.e., using only the three third gaps I, a bend radius of articulation joint 50 is reduced, thereby allowing articulation joint 50 to bend in smaller spaces. It will be understood that while second link section 54 is shown as being capable of bending in three directions, second link section 54 may be capable of bending in only two directions in some examples.

As described hereinabove, articulation or bending of the articulation joint 50 may be controlled by actuation elements 12. In particular, the articulation joint 50 may include four actuation elements, which may control bending of the articulation joint 50 in four directions. For example, by tightening/tensioning the articulating element 12 extending along the second side 58*b* and loosening the articulating element 12 extending along the first side 58*a*, the articulation joint 50 may bend toward the second side 58*b*, as depicted in FIG. 4C.

Referring still to FIGS. 4A-4D, the articulation joint 50 may include a locking wire 60. The locking wire 60 may extend through the lumen 32 and may be attached to and terminate at link 50*b*' of the adjacent links 50*b* of the second link section 54. As depicted, the link 50*b*' may be the first link distal to, and directly adjacent, the first link section 52. In some embodiments, the locking wire 60 may extend through the actuation holes 25 (depicted, for example, in FIGS. 2 and 3). In particular, one or more of the actuation holes 25 may be sized to fit both the locking wire 60 and one of the actuation elements 12, and the locking wire 60 and the articulating element 12 may extend through the same articulation hole 25.

The locking wire may be disposed adjacent the flat contact surfaces 53, e.g. along the second side 58*b* and terminate inside link 50*b*' at point 62. Accordingly, the locking wire 60 may selectively prevent articulation about the flat contact surfaces 53, e.g. toward the first side 58*a*, when pulled taught. The movement of the second link section 54 and the third link section 56 may be unaffected by the locking wire 60. In other words, when the locking wire 60 is tightened/tensioned, the configuration of the articulation joint 50 depicted in FIG. 4A may be prevented, and the articulation joint 50 may instead be limited to approximately 90 degrees of bending in each direction as depicted in FIG. 4D. This limitation on the movement of the first section of links 52 may enable the articulation joint 50 to bend more easily in smaller spaces. When the locking wire 60 is loosened, the locking wire 60 may allow movement of the adjacent links 50*a* toward the first side 58*a*, so that the articulation joint 50 may attain the configuration shown in FIG. 4A. As will now be appreciated, the locking wire 60 may allow selective control of the range of articulation of the articulation joint 50, especially toward the first side 58*a*. This may enable easier transition of the articulation joint 50 between large and small spaces where available room for articulation may vary.

A method of using the endoscope 10 may include inserting the endoscope 10 into a subject's mouth and guiding the tip 30 and articulation joint 50 into a stomach of a subject via an esophagus of the subject. The articulation joint 50 may then be actuated by moving or rotating the actuating device 42 and/or 43. As described hereinabove, moving or rotating the actuating devices 42 and 43 may tighten or loosen the actuating elements 12 which may, in turn, actuate (bend) the articulation joint 50. In particular, the method may include actuating the articulation joint 50 such that the tip 30 faces the fundus, or the top of the subject's stomach (e.g., such that the articulation joint 50 is arranged as depicted in FIG. 4A). This full range of articulation may enable a camera, which may be disposed within the tip 30, to view all areas within the stomach.

The user of the endoscope 10 may then, in some examples, desire to view portions of the GI tract distal to the stomach, for example the duodenum. The user may first straighten the articulation joint 50 (the configuration shown in FIG. 4B), by relieving tension on actuating elements 12. The tip 30 and the articulation joint 50 then may be advanced into the duodenum. To view tissue at a side of the duodenum (which is a more confined space than the stomach), the method may include moving or rotating the actuation device 41 to tighten the locking wire 60. This limits articulation of the tip 30 and the articulation joint 50 to the arrangements depicted in FIGS. 4B, 4C, and 4D. Actuation elements 12 then may be tensioned to achieve one or more of these arrangements. Accordingly, the tip 30 and the articulation joint 50 may be advanced into, and articulated within, the duodenum, more easily.

As will now be appreciated, the above-described endoscope 10 and the above-described exemplary method of use may enable visualization of the stomach and the duodenum with a single device, i.e. the endoscope 10. This may be easier and faster than using a first device, such as a gastroscope, to view the stomach and a second device, such as a duodenoscope, to view the duodenum.

Figure 5:
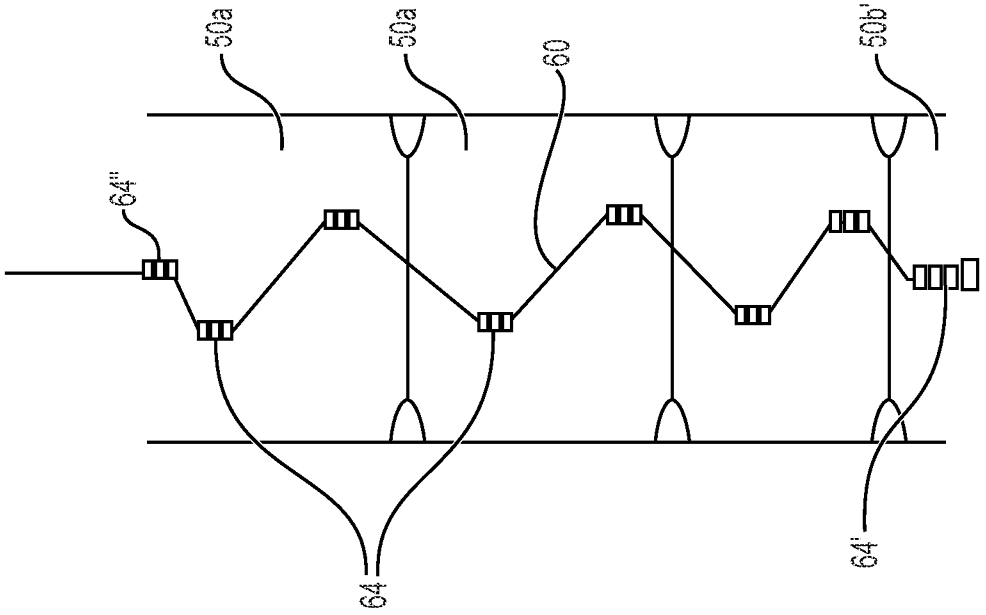
FIG. 5 is a cross-section of the articulation joint of FIG. 3 along the section B-B.

FIG. 5 shows a cross sectional view of the articulation joint 50 of FIG. 3 taken at B-B, showing the internal portion of first section of links 52, the proximalmost link 50*b*' of second section of links 54, and the locking wire 60. In this embodiment, the locking wire 60 may extend through the lumen 32 and adjacent the flat contact surfaces 53 but may not extend through one of the actuation holes 25. In particular, in some such embodiments, the locking wire 60 may instead extend through wire supports 64, which may be eyelets, springs, or other suitable structure. The wire supports 64 may be arranged on alternating sides of the actuation holes 25 (to the side of the axis going through actuation holes 25 situated at same side of joint 50). The locking wire 60 may terminate at a terminal support 64' along the same axis as the actuation holes at that side of the joint 50. In addition, the proximalmost support 64" lies along the same axis as the actuation holes at that side of the joint 50. In this way, the locking wire 60, when extending though the wire supports 64, may be arranged in a zig-zag pattern along the adjacent links 50*a* and 50*b*'. This may be beneficial in some embodiments as it may keep locking wire 60 out of the way of wires 12 or other structure and/or enable stronger restriction of the movement of the first section of links 52 when the locking wire 60 is tightened.

It will be apparent to those skilled in the art that various modifications and variations can be made to the disclosed device without departing from the scope of the disclosure. For examples, the configuration of gaps and links and the bend angles may be altered to suit any medical device. It will be understood that the bend angles, sizes of each gap, and/or the number of gaps and links are not limited to the examples described herein. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An articulation joint for a medical device, comprising:

a proximal longitudinal section defining a lumen therethrough and having proximal articulation links, each proximal articulation link having a contact surface abutting a contact surface of an adjacent proximal articulation link when the articulation joint is in a straight configuration, to limit bending of the proximal longitudinal section to only a first direction;

a distal longitudinal section distal to the proximal longitudinal section and having distal articulation links, wherein the distal longitudinal section is configured to bend in the first direction;

four articulation wires extending through the proximal longitudinal section and the distal longitudinal section, where the four articulation wires control bending of the articulation joint; and a single locking wire extending through the lumen adjacent the contact surfaces of the proximal articulation links, wherein a distal end of the locking wire is fixed to a distal articulation link, and wherein tensioning of only the single locking wire prevents bending of the proximal longitudinal section in the first direction and allows bending of the distal longitudinal section in the first direction.

2. The articulation joint of claim 1, wherein a gap is defined between adjacent proximal articulation links, the gap being disposed on a side of the proximal longitudinal section opposite a side having the contact surfaces.

3. The articulation joint of claim 2, wherein a spring connects adjacent proximal articulation links along surfaces of the adjacent proximal articulation links between the contact surfaces and the gap.

4. The articulation joint of claim 1, wherein a plurality of the distal articulation links are distal of the locking wire, and tensioning of the locking wire does not straighten or bend the plurality of the distal articulation links.

5. The articulation joint of claim 1, wherein the locking wire is arranged in a zig-zig pattern within the lumen.

6. The articulation joint of claim 5, wherein each proximal articulation link includes a wire support, wherein the wire supports of adjacent proximal articulation links are circumferentially offset from one another, and wherein the locking wire extends through each wire support.

7. The articulation joint of claim 1, wherein the four articulation wires control bending of the articulation joint in the first direction, a second direction, a third direction, and a fourth direction.

8. The articulation joint of claim 7, further comprising actuation holes coupled to each of the proximal articulation links and the distal articulation links, wherein the articulation wires extend through the actuation holes.

9. The articulation joint of claim 8, further comprising springs, the springs defining the actuation holes.

10. The articulation joint of claim 8, wherein at least one of the actuation holes accommodates the locking wire and one of the articulation wires.

11. The articulation joint of claim 1, wherein a maximum combined bending of the proximal longitudinal section and the distal longitudinal section in the first direction when the locking wire is not tensioned is approximately 180 degrees, and a maximum combined bending of the proximal longitudinal section and the distal longitudinal section in the first direction when the locking wire is tensioned is approximately 90 degrees.

12. The articulation joint of claim 1, wherein the proximal longitudinal section is straight when the locking wire is tensioned.

13. An articulation joint for a medical device, comprising:

a proximal longitudinal section defining a lumen therethrough and having proximal articulation links, each proximal articulation link having a flat contact surface abutting a flat contact surface of an adjacent proximal articulation link when the articulation joint is in a straight configuration, to limit bending of the proximal longitudinal section to only a first direction;

a distal longitudinal section distal to the proximal longitudinal section and having distal articulation links, wherein the distal longitudinal section is configured to bend in the first direction and a second direction opposite the first direction;

a single locking wire extending through the lumen adjacent the contact surfaces of the proximal articulation links, wherein a distal end of the locking wire is fixed to a distal articulation link, and tensioning of only the single locking wire prevents bending of the proximal longitudinal section in the first direction and allows bending of the distal longitudinal section in the first direction; and a first wire and a second wire each extending through the lumen, the first wire for controlling bending of the distal longitudinal section in the first direction, and the second wire for controlling bending of the distal longitudinal section in the second direction, wherein each of the first wire and the second wire extends distally past the distal end of the single locking wire.

14. The articulation joint of claim 13, wherein the distal longitudinal section is configured to bend in a third direction and a fourth direction opposite the third direction, and the articulation joint further comprises a third wire and a fourth wire each extending through the lumen, the third wire for controlling bending of the distal longitudinal section in the third direction, and the fourth wire for controlling bending of the distal longitudinal section in the fourth direction, wherein each of the third wire and the fourth wire extends distally past the distal end of the single locking wire.

15. The articulation joint of claim 13, wherein the single locking wire is arranged in a zig-zig pattern within the lumen.

16. An articulation joint for a medical device, comprising:

a proximal longitudinal section defining a lumen therethrough and having proximal articulation links, each proximal articulation link having a contact surface abutting a contact surface of an adjacent proximal articulation link when the articulation joint is in a straight configuration, to limit bending of the proximal longitudinal section to only a first direction;

a distal longitudinal section distal to the proximal longitudinal section and having distal articulation links, wherein the distal longitudinal section is configured to bend in the first direction and a second direction opposite the first direction; and a locking wire extending through the lumen adjacent the contact surfaces of the proximal articulation links, wherein a distal end of the locking wire is fixed to a distal articulation link, and tensioning of the locking wire prevents bending of the proximal longitudinal section in the first direction, allows bending of the distal longitudinal section in the first direction, and retains the proximal longitudinal section in a straight configuration, wherein the locking wire is arranged in a zig-zig pattern within the lumen, wherein the proximal longitudinal section and the distal longitudinal section can combine to bend 180 degrees in the first direction when the locking wire is not tensioned, and a maximum combined bending of the proximal longitudinal section and the distal longitudinal section in the first direction when the locking wire is tensioned is approximately 90 degrees.

17. The articulation joint of claim 16, further comprising four articulation wires operable to control bending of the articulation joint in the first direction, the second direction, a third direction, and a fourth direction.

18. The articulation joint of claim 16, wherein each proximal articulation link includes a wire support, wherein the wire supports of adjacent proximal articulation links are circumferentially offset from one another, and wherein the locking wire extends through each wire support.

19. The articulation joint of claim 16, wherein the locking wire is a single locking wire, wherein tensioning of only the single locking wire prevents bending of the proximal longitudinal section in the first direction.

* * * * *